United States Patent [19]

Aberg

[11] Patent Number: 5,057,305

[45] Date of Patent: * Oct. 15, 1991

[54] TOOTH CLEANING TABLET

[75] Inventor: Torwald Aberg, Stockholm, Sweden

[73] Assignee: Dentab, Inc., Stamford, Conn.

[ * ] Notice: The portion of the term of this patent subsequent to Jun. 28, 2005 has been disclaimed.

[21] Appl. No.: 146,910

[22] Filed: Jan. 22, 1988

Related U.S. Application Data

[63] Continuation of Ser. No. 928,571, Nov. 10, 1986, Pat. No. 4,753,792, which is a continuation of Ser. No. 765,158, Aug. 13, 1985, abandoned.

[30] Foreign Application Priority Data

Aug. 21, 1984 [GB] United Kingdom ................. 8421226

[51] Int. Cl.$^5$ .......................... A61K 9/46; A61K 7/18; A61K 33/16
[52] U.S. Cl. ........................................ 424/44; 424/49; 424/52
[58] Field of Search .............................. 424/44, 49, 52

[56] References Cited

U.S. PATENT DOCUMENTS

| | | | |
|---|---|---|---|
| 1,262,888 | 4/1918 | Westlake | 424/44 |
| 3,116,208 | 12/1963 | Emond | 424/49 |
| 3,151,028 | 9/1964 | Hay et al. | 424/49 |
| 3,431,339 | 3/1969 | Gyarmathy et al. | 424/49 |
| 3,629,468 | 12/1971 | Andersen | 424/44 |
| 3,962,417 | 6/1976 | Howell | 424/52 |
| 4,267,164 | 5/1981 | Yeh et al. | 424/44 |
| 4,308,252 | 12/1981 | Tomaich et al. | 424/52 |
| 4,592,855 | 6/1986 | Gioffre et al. | 252/89.1 |
| 4,753,792 | 6/1988 | Aberg | 424/44 |
| 4,818,518 | 4/1989 | Gioffre et al. | 424/44 |

FOREIGN PATENT DOCUMENTS

| | | |
|---|---|---|
| 284579 | 6/1966 | Australia . |
| 2051499 | 4/1971 | Fed. Rep. of Germany . |
| 1259342 | 1/1972 | United Kingdom . |
| 2071493A | 9/1981 | United Kingdom . |
| 2163348A | 2/1986 | United Kingdom . |

*Primary Examiner*—Shep K. Rose
*Attorney, Agent, or Firm*—F. Eugene Davis IV

[57] ABSTRACT

A tooth cleaning tablet, which tablet is such that when it is chewed in a person's mouth it forms a paste and so enables the person to effect a tooth cleaning operation as though using toothpaste.

7 Claims, No Drawings

TOOTH CLEANING TABLET

This application is a continuation of application Ser. No. 928,571 filed Nov. 10, 1986, now U.S. Pat. No. 4,753,792, which is a continuation of Ser. No. 765,158 filed Aug. 13, 1985, now abandoned.

This invention relates to a tooth cleaning tablet.

The world wide practice of tooth cleaning is usually effected with tooth paste. The tooth paste is sold in tubes of different sizes but there invariably occurs the problem of squeezing the last drop of tooth paste from the tube to avoid wastage. To a lesser extent there also invariably occurs the problem of where and how to squeeze the tube during use in order to ensure the easy dispensation of the tooth paste when there is not much of it left in the tube.

It is an aim of the present invention to obviate or reduce the above mentioned problems.

Accordingly, the present invention provides a tooth cleaninq tablet, which tablet is such that when it is chewed in a person's mouth it forms a paste and so enables the person to effect a tooth cleaning operation as though using tooth paste.

The advantages of the tooth cleaning tablet over tooth paste are legion. For example, packaging of tablets can virtually be changed at will to meet different modes of distribution and different markets. The many and various techniques used for packaging and selling medicinal tablets can be employed for packaging and selling the tooth cleaning tablets. Thus, the tablets can be trapped between two layers of metallic foil and sold in packets in boxes, with for example four or six tablets to a packet. Alternatively, the tablets can be pressed through metallic foil from individual compartments in a plastics base. Still further, the tablets can be placed in loose tubes, or individually wrapped, or wrapped in columns. For travelling purposes, a plurality of the tablets may be provided in a tube that also houses a tooth brush of the type that can be housed in a tube for storage or travel.

The tooth cleaning tablets may be cheaper to produce and package than conventional tooth paste. Storing of the tablets prior to sale may be easier. Portion control and distribution in institutions such as hospitals, prisons and nursery schools becomes easily possible.

The tablets may be easily distributed through vending machines, and this is of obvious benefit to persons using hotels, airlines and shipping lines. Indeed, simply by using different flavours and/or colours, a hotel, airline or shipping line could have its own individual tablets. The tablets could be sold or given away with the compliments of the management. Also, if desired, the tablets could be produced in a colour and/or a shape that was attractive to children to give them an incentive to use the tablets and so clean their teeth.

Usually, the tooth cleaning tablet will be water free.

The tablet is preferably a hard brittle tablet. Such a tablet is crushed as it is chewed in a person's mouth. It is to be appreciated that the tablet need not be brittle and that it could be in another form such as that of a solidified gel.

Preferably, the tablet comprises:
(i) a polishing agent
(ii) a swelling agent
(iii) a foaming agent
(iv) a filling agent
(v) a taste-giving agent
(vi) a wetting agent, and
(vii) a lubricative agent.

The polishing agent may be a phosphate, a carbonate or a polymer.

The phosphate may be a metal phosphate. Typical metal phosphates are sodium metaphosphate, potassium metaphosphate, calcium pyrophosphate, magnesium orthophosphate, trimagnesium phosphate, tricalcium phosphate and dicalcium phosphate.

Typical carbonates are calcium carbonate and sodium bicarbonate.

The swelling agent may be sodiumcarboxymethylcellulose, irish moss, tragacanth gum, accaceia gum, gelatin, an alginic compound, methylcellulose polyvinylpyrrolidon or xanthan gum. The xanthan gum is preferably that sold under the Trade Mark KELTROL.

The alginic compound may be an alginic acid, an alginic salt, or an alginic ester.

The tooth cleaning tablet may contain more than one foaming agent if desired.

The foaming agent may be at least one compound selected from the group consisting of sodium bicarbonate, calcium bicarbonate, citric acid and tartaric acid.

The filling agent may be a waxy polyethylene glycol such for example as that known as carbowax 6000 or carbowax 4000.

The filling agent may alternatively be a hexitol component such for example as mannitol or sorbitol.

Still further, the filling agent may be lactat, starch or a silicon oxide.

The tooth cleaning tablet may contain more than one taste-giving agent if desired. Any taste-giving agent may be employed.

Preferably, the taste-giving agent is at least one compound selected from the group consisting of menthol, peppermint and cyklamate.

The wetting agent may be an oxyethylenoxypropylene polymer, a polyoxyethylensorbitan derivative from a fatty acid, or sodium laurylsulphate. The derivative from the fatty acid may be polyoxyethylensorbitanstearate. A presently preferred wetting agent is the sodium laurylsulphate sold under the trade mark Texapon K12.

The tooth cleaning tablet may also contain an aroma-giving agent, for example peppermint oil or spearmint oil.

The tooth cleaning tablet may also contain a plaque indicating agent.

The tooth cleaning tablet may also contain a tooth protective agent which acts to reduce tooth decay. Usually, the tooth protective agent will improve the resistance of the teeth to attack by acids. The tooth protective agent may also kill plaque producing germs. The tooth protective agent may be sodium fluoride, sodium monofluorophosphate, a chlorhexidine salt or hexachlorophane. The sodium fluoride may be used in amounts up to 0.3% by volume of the tablet. The sodium monofluorophosphate may be used in amounts up to 1% by volume of the tablet.

The tooth cleaning tablet may also contain a sweetening agent. The sweetening agent may be sugar or a sugar based substance. A replacement substance for sugar may advantageously be employed such for example as zilotol.

Embodiments of the invention will now be given with reference to the accompanying Examples.

EXAMPLE 1

A water-free tooth cleaning tablet was produced using methods known in themselves for producing medicinal tablets. The tooth cleaning tablet was produced in moisture-free air and it had the following composition:

| | | |
|---|---|---|
| 0.213 g | Tricalciumphosphate | Polishing agent |
| 0.053 g | Keltrol | Swelling agent |
| 0.08 g | Sodium bicarbonate | Foaming agent |
| 0.032 g | Citric Acid | Foaming agent |
| 0.192 g | Sorbitoleum | Filling agent |
| 0.04 g | Cyklamate | Taste-giving agent |
| 0.010 g | Texapon K12 | Wetting agent |
| 0.005 g | Magnesium Stearate | Lubricative agent |
| 2% | Natural Aroma | Aroma-giving agent |
| 0,625 g | | |

The Natural Aroma was present as 2% by weight. The aroma-giving agent may also be an agent which contributes to the taste of the tooth cleaning tablet. The produced tooth cleaning tablet was hard and brittle. It was chewed in the mouth for approximately 15 seconds during which time it firstly became crushed and secondly formed a paste. The formation of the paste enabled the person chewing the tablet to stop chewing and to effect a tooth cleaning operation as though using tooth paste. After mouth rinsing, the teeth were found to be at least as satisfactorily cleaned as with conventional tooth paste and some persons found the tablet more pleasant to use than tooth paste.

EXAMPLE 2

A water-free tooth cleaning tablet was produced to have all the ingredients of the tablet of Example 1, and it also had a plaque-indicating agent. On chewing of the tablet to form the paste, the plaque-indicating agent was effective to indicate those areas of the teeth where plaque was present and which thus required special cleaning.

It is to be appreciated that the Examples hereinbefore given have been given for purposes of illustration only and they are not intended to be limiting in any way. Thus, more than one of each of the polishing, swelling, filling, taste-giving, wetting, lubricative and aroma-giving agents listed in Example 1 may be employed if desired.

I claim:

1. A tooth cleaning tablet forming a self-foaming paste when chewed in the mouth comprising by weight:
   A. about 75% polishing and filing agent; and,
   B. about 18% of a carbon dioxide producing composition.

2. The tooth cleaning tablet of claim 1 wherein said polishing agent comprises about 34% of the tablet.

3. The tooth cleaning table of claim 2 and said tablet further comprises:
   C. about 8.5% of a swelling agent; and,
   C. about 1.5% of a wetting agent.

4. The method of tooth cleaning comprising:
   A. placing a tablet according to claim 1 in the mouth;
   B. chewing the tablet to form a self-foaming paste in the mouth;
   C. swishing the paste around and through the interstices between the teeth to mechanically clean the teeth; and
   D. swallowing the excess paste.

5. A tooth cleaning tablet forming a self-foaming paste when chewed in the mouth comprising by weight:
   A. about 75% polishing and filing agents; and,
   B. about 18% of a gas producing composition.

6. The tooth cleaning tablet of claim 5 wherein said polishing agent comprises about 34% of the tablet.

7. The tooth cleaning tablet of claim 6 and said tablet further comprises:
   C. about 8.5% of a swelling agent; and,
   D. about 1.5% of a wetting agent.

* * * * *